(12) United States Patent
Maignan

(10) Patent No.: US 6,395,867 B1
(45) Date of Patent: May 28, 2002

(54) POLYMERS WITH THIOL TERMINAL FUNCTION

(75) Inventor: Jean Maignan, Tremblay en France (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 09/402,201

(22) PCT Filed: Mar. 26, 1998

(86) PCT No.: PCT/FR98/00620

§ 371 Date: Jan. 21, 2000

§ 102(e) Date: Jan. 21, 2000

(87) PCT Pub. No.: WO98/44024

PCT Pub. Date: Oct. 8, 1998

(30) Foreign Application Priority Data

Apr. 3, 1997 (FR) ............................................. 97/04085

(51) Int. Cl.⁷ ............................................. C08G 69/08
(52) U.S. Cl. ..................... 528/310; 528/360; 528/373; 528/377
(58) Field of Search ............................... 528/310, 360, 528/373, 377

(56) References Cited

U.S. PATENT DOCUMENTS

| | | | |
|---|---|---|---|
| 4,289,872 A | 9/1981 | Denkewalter et al. | 528/328 |
| 4,360,646 A | 11/1982 | Denkewalter et al. | 525/420 |
| 4,507,466 A | 3/1985 | Tomalia et al. | 528/332 |
| 4,558,120 A | 12/1985 | Tomalia et al. | 528/363 |
| 4,568,737 A | 2/1986 | Tomalia et al. | 528/332 |
| 4,587,329 A | 5/1986 | Tomalia et al. | 528/363 |
| 4,631,337 A | 12/1986 | Tomalia et al. | 528/391 |
| 4,694,064 A | 9/1987 | Tomalia et al. | 528/332 |
| 5,196,502 A | 3/1993 | Turner et al. | 528/272 |
| 5,214,122 A | 5/1993 | Turner et al. | 528/272 |

FOREIGN PATENT DOCUMENTS

| | | |
|---|---|---|
| EP | 0 234 408 | 9/1987 |
| EP | 0 247 629 | 12/1987 |
| EP | 0 556 871 | 8/1993 |
| EP | 0 682 059 | 11/1995 |
| EP | 0 684 044 | 11/1995 |
| FR | 2 734 268 | 11/1996 |
| WO | WO 92/14543 | 9/1992 |
| WO | WO 93/14147 | 7/1993 |
| WO | WO 93/17060 | 9/1993 |
| WO | WO 95/02008 | 1/1995 |
| WO | WO 95/02397 | 1/1995 |
| WO | WO 95/34595 | 12/1995 |
| WO | WO 96/12754 | 5/1996 |
| WO | WO 96/14345 | 5/1996 |
| WO | WO 96/14346 | 5/1996 |

OTHER PUBLICATIONS

B.I. Voit, "Dendritic polymers: from aesthetic macromolecules to commercially interesting materials", Acta Polymers, 46, 1995, pp. 87–99, The month in the date of publication is not available.

Donald A. Tomalia et al., "Starbust Dendrimers: Molecular–Level Control of Size, Shape, Surface, Chemistry Topology, and Flexibility form Atoms to Macroscopic Matter", Angew. Chem. Int. Ed. Engl. 29, 1990, pp. 138–175, The month in the date of publication is not available.

Nicole Ardoin et al., "Molecular trees: from syntheses towards applications", Bull. Soc. Chim. Fr, 132, 1995, pp. 875–909, The month in the date of publication is not available.

K.E. Uhrich et al., "One–Pot Synthesis of Hyperbranched Polyethers", Macromolecules, 25, 1992, pp. 4583–4587, The month in the date of publication is not available.

Craig J. Hawker et al., "Preparation of Polymers with Controlled Molecular Architecture. A New Covergent Approach to Dendritic Macromolecules", J. Am. Chem. Soc., 112, 1990, pp. 7638–7647, The month in the date of publication is not available.

Michael Slany et al., "Dendrimer Surface Chemistry. Facile Route to Polyphosphines and Their Gold Complexes", J. Am. Chem. Soc., 117, 1995, pp. 9764–9765, The month in the date of publication is not available.

C.J. Hawker, "One–Step Synthesis of Hyperbranched Dendritic Polyesters", J. Am. Chem. Soc., 113, 1991, pp. 4583–4588, The month in the date of publication is not available.

English language Derwent Abstract of FR 2 734 268, May 19, 1995.

Primary Examiner—Terressa M. Boykin
(74) Attorney, Agent, or Firm—Finnegan, Henderson, Farabow, Garrett & Dunner, L.L.P.

(57) ABSTRACT

A polymer chosen from hyperbranched polymers and dendrimers containing at least one functional group of formula (I):

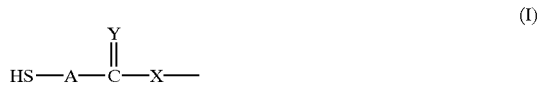

in which: Y is chosen from an oxygen atom and an NH group; A is chosen from linear, branched and cyclic, saturated and unsaturated $C_1$–$C_{12}$ alkanediyl groups, wherein said alkanediyl groups may or may not be interrupted by at least one heteroatom, and further wherein said alkanediyl group may or may not be substituted with at least one function chosen from: -amino groups $NH_2$ and salts thereof with inorganic acids or organic acids, -acylamino groups NH—COR, in which R is chosen from linear, branched and cyclic, saturated and unsaturated $C_1$–$C_{10}$ alkyl groups, -$C_1$–$C_{10}$ alkylamino groups, -carboxylic acid, and -$C_1$–$C_{10}$ esters; and X is chosen from nucleophilic groups, methods for preparing the polymer and using the polymer as an antioxidant is disclosed.

33 Claims, No Drawings

POLYMERS WITH THIOL TERMINAL FUNCTION

The invention relates to novel hyperbranched dendrimers and polymers containing thiol functional groups, to a process for their preparation and to the use of these hyperbranched dendrimers and/or polymers as ancioxidants.

Many hyperbranched polymers and dendrimers have already been described. Reference may be made, for example to: D. A. Tomalia et al., Angew. Chem. Int. Engl. 29 (1990) 138–175; N. Ardoin and D. Astruc, Bull. Soc. Chim. Fr. (1995) 132, 875–909; B. I. Voit, Acta Polymer, 46, 87–99 (1995).

The possibility of preparing dendrimers containing thiol end groups has been envisaged by certain authors, such as, for example, D. A. Tomalia in U.S. Pat. No. 4,587,329 and EP-A-234,408, although this preparation has never been effectively carried out, nor have the surprising properties, demonstrated by the Applicant, of these molecules been mentioned or suggested in the prior art.

In addition, the process for preparing hyperbranched polymers and dendrimers containing thiol functional groups is novel and it has many advantages, among which are the good synthetic yield, the use of commercially available starting materials and the ease of implementation.

Hyperbranched polymers are molecular constructions having a branched structure, generally about a core. Their structure generally lacks symmetry: the monomer or base units involved in the construction of the hyperbranched polymer can be of varied nature and they are distributed non-uniformly. The branches in the polymer can be of varied nature and length. The number of base units, or monomers, can be different according to the different branching. While remaining asymmetrical, hyperbranched polymers can have: an extremely branched structure, around a core; successive generations or layers of branching; a layer of end chains.

Hyperbranched polymers are generally obtained from the polycondensation of one or more monomers ABx, A and B being reactive groups capable of reacting together, x being an integer greater than or equal to 2, but other preparation processes can be envisaged. Hyperbranched polymers are characterized by their degree of polymerization DP=1−b, b being the percentage of non-terminal functional groups in B which have not reacted with a group A. Since the condensation is non-systematic, in contrast with the synthesis of dendrimers, the degree of polymerization is less than 100%. Usually, by the known synthetic methods, DP is between 15 and 90%. An end group T can be reacted with the hyperbranched polymer to obtain a specific functionality at the end of the chains.

Such polymers are described in particular in B. I. Voit, Acta Polymer, 46, 87–99 (1995); EP-682,059, WO-96/14346; WO-96/14345; WO-96/12754.

Several hyperbranched polymers can be combined together, by means of a covalent bond or another type of bonding, via their end groups. Such so-called "bridged" polymers come within the definition of the hyperbranched polymers according to the present invention.

Dendrimers are highly branched polymers and oligomers that are also known; they have a well-defined chemical structure and are said to be "perfect" hyperbranched polymers. As a general rule, dendrimers comprise a core, a determined number of generations of branches, or spindles, and terminal groups. The generations of spindles consist of structural units which are identical for the same generation of spindles and which can be identical or different for different generations of spindles. The generations of spindles extend radially in a geometrical progression from the core. The terminal groups of a dendrimer of the $N^{th}$ generation are the terminal functional groups of the spindles of the $N^{th}$ generation or terminal generation. Such polymers are described in particular in D. A. Tomalia, A. M. Naylor and W. A. Goddard III, Angewandte Chemie, Int. Ed. Engl. 29, 138–175 (1990); C. J. Hawker and J. M. J. Frechet, J. Am. Chem. Soc., 112, 7638 (1990); B. I. Voit, Acta Polymer, 46, 87–99 (1995); N. Ardoin and D. Astruc. Bull. Soc. Chim. Fr. 132, 875–909 (1995).

Dendrimers can also, more particularly, be defined by the formula (DI) below:

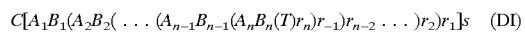

$$C[A_1B_1(A_2B_2(\ldots(A_{n-1}B_{n-1}(A_nB_n(T)r_n)r_{-1})r_{n-2}\ldots)r_2)r_1]s \quad (DI)$$

in which:

C represents the core, linked by a number s of functional groups to s spindles $A_1B_1$ via the groups $A_1$;

s is an integer greater than or equal to 1 and less than or equal to the number of functional groups in C;

for each spindle $(A_iB_i)$ (i=1, 2 ... n), the group $B_i$ is linked to $r_i$ groups $A_{i+1}$ of a spindle $(A_{i+1}B_{i+1})$;

each group $A_i$ (i>2) is linked to a single group $B_{i+1}$ of the spindle $(A_{i+1}B_{i+1})$;

$r_i$ (i=1, 2 ... n−1) represents the number of functional groups in the group $B_i$ belonging to the spindle $(A_iB_i)$, ri being an integer greater than or equal to 2;

the index i (i=1, 2 ... n) is an integer which denotes the generation of each spindle;

the spindle of $n^{th}$ generation $A_nB_n$ is linked chemically to a number $r_n$ of terminal groups T, $r_n$ being an integer greater than or equal to zero.

The dendrimer definition given above includes molecules containing symmetrical branching; it also includes molecules containing non-symmetrical branching such as, for example, dendrimers whose spindles are lysine groups, in which the branching of one generation of spindles onto the preceding generation takes place on the amines a and e of lysine, which leads to a difference in the length of the spindles for the different branching.

Dense star polymers, starburst polymers and rod-shaped dendrimers are included in the present definition of dendrimers. The molecules known as arborols and cascade molecules also fall within the definition of dendrimers according to the present invention.

Several dendrimers can be combined together, via a covalent bond or another type of bond, via their terminal groups in order to give species known as "bridged dendrimers" or "dendrimer aggregates". Such species are included in the definition of dendrimers according to the present invention.

Dendrimers can be in the form of a set of molecules of the same generation, these being so-called monodispersed sets; they can also be in the form of sets of different generations, which are known as polydispersed sets. The definition of dendrimers according to the present invention includes monodispersed sets as well as polydispersed sets of dendrimers.

The subject of the invention is novel polymers chosen from hyperbranched polymers and dendrimers, characterized in that they contain functional groups corresponding to formula (I):

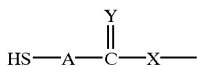
(I)

in which:
Y represents an oxygen atom or an NH group, preferably Y=O,
A represents a linear, branched or cyclic, saturated or unsaturated $C_1$–$C_{12}$ alkanediyl group;
this alkanediyl group can optionally be interrupted by one or more hetero atoms, such as O or N;
this alkanediyl group can optionally be substituted with one of the following functions
amino: —$NH_2$, optionally in the form of a salt of an inorganic or organic acid,
acylamino: —NH—COR, in which R represents a linear, branched or cyclic, saturated or unsaturated $C_1$–$C_{10}$ alkyl group,
carboxylic acid,
$C_1$–$C_{10}$ ester;
X represents a nucleophilic group, preferably:
an oxygen atom
or
a group —NR'— in which R' is chosen from a hydrogen atom; a linear or branched, saturated or unsaturated $C_1$–$C_6$ alkyl group; a linear or branched, saturated or unsaturated $C_1$–$C_6$ mono- or polyhydroxyalkyl group; a $C_1$–$C_6$ aminoalkyl group or a polyalkyleneimine group.

For example, A can be a methylene, ethylene, propylene, methylpropylene, ethylpropylene, tetramethylene, pentamethylene, hexamethylene, phenylene, phenyldiyl, etc. group.

Advantageously, A represents a radical corresponding to one of the formulae (a) to (d) below:

—$CHR^1$—$CHR^2$—$CHR^3$— (a)

—$CHR'^1$—$CHR'^2$—$CHR'^3$—$CHR'^4$— (b)

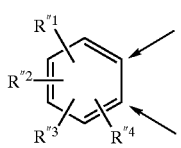
(c)

—$(CHR'''^1)_k$—$(CHR'''^2)$—$CH(CO_2H)$—NH— (d)

in which $R^1$, $R^2$, $R^3$, $R'^1$, $R'^2$, $R'^3$, $R'^4$, $R'''^1$ and $R'''^2$, which may be identical or different, represent: a hydrogen atom, a linear, branched or cyclic, saturated or unsaturated $C_1$–$C_6$ alkyl radical, an amino radical —$NH_2$, a carboxylic acid radical —COOH, a $C_1$–$C_{10}$ alkylamino radical; $R''^1$, $R''^2$, $R''^3$ and $R''^4$, which may be identical or different, represent: a hydrogen atom, a linear or branched, saturated or unsaturated $C_1$–$C_4$ alkyl radical, the arrows indicating the positions of the substitutions in formula (c), k is an integer, preferably k=0 or 1.

Preferably, A is chosen from:
—$CH_2$—CH ($CO_2H$) —NH— and Y=O
—$(CH_2)_2$—$(CH_3CONH)$ CH— and Y=O
—$(CH_2)_3$— and Y=O or Y=NH Advantageously, A is the trimethylene radical —$CH_2$—$CH_2$—$CH_2$—, and Y=O, the compound according to the invention corresponding in this case to formula (II) below:

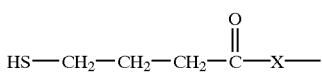
(II)

in which:
X represents a nucleophilic group, preferably:
an oxygen atom
or
a group —NR'— in which R' is chosen from a hydrogen atom; a linear or branched, saturated or unsaturated $C_1$–$C_6$ alkyl group; a linear or branched, saturated or unsaturated mono- or polyhydroxyalkyl group; a $C_1$–$C_6$ aminoalkyl group or a polyalkyleneimine group.

Preferably, according to the invention, X is chosen from: an oxygen atom and an NH group.

In the case of dendrimers, the nucleophilic group X is generally an end functional group. In the case of hyperbranched polymers such as, for example, polyethyleneimine, the group X can be a secondary amine found on one of the branches of the polymer without being in the end position.

Advantageously, according to the invention, at least 10%, in numerical terms, of the groups X of the hyperbranched polymer or of the dendrimer are grafted with a functional group:

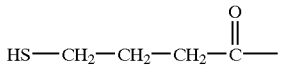

and even more preferably at least 40%. The percentage of thiol functional groups relative to the total number of functional groups X in the hyperbranched polymer or the dendrimer which are capable of being substituted by a group:

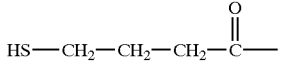

is adapted as a function of the other characteristics of the hyperbranched polymer or the dendrimer, in particular the number of generations and the nature of the spindles, and as a function of the expected properties, in particular the solubility of the hyperbranched polymer or of the dendrimer. Such adaptations are within the scope of a person skilled in the art by simple tests.

The subject of the invention is also a first process for preparing hyperbranched polymers and dendrimers containing thiol end groups, this process being characterized in that a starting polymer, chosen from hyperbranched polymers and dendrimers in which the end groups or chains contain a nucleophilic function, is reacted with a thiolactone or an iminothiolane according to the following reaction scheme:

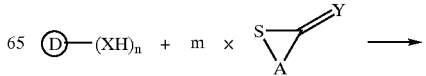

-continued

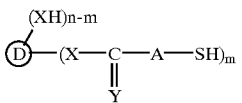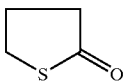

in which

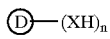

represents a dendrimer or a hyperbranched polymer containing n functions XH, as defined above, m is an integer m<n and A represents a radical corresponding to one of the formulae (a) to (d) below:

—CHR$^1$—CHR$^2$—CHR$^3$—     (a)

—CHR$'^1$—CHR$'^2$—CHR$'^3$—CHR$'^4$—     (b)

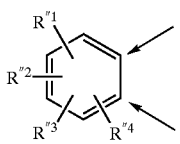     (c)

—(CHR$'''^1$)$_k$—(CHR$'''^2$) —CH(CO$_2$H) —NH—     (d)

in which R$^1$, R$^2_1$, R$^3$, R$'^1$, R$'^2$, R$'^3$, R$'^4$, R$'''^1$ and R$'''^2$, which may be identical or different, represent: a hydrogen atom, a linear or branched, saturated or unsaturated C$_1$–C$_6$ alkyl radical, an amino radical —NH$_2$, a carboxylic acid radical —COOH, a C$_1$–C$_{10}$ alkylamino radical; R$''^1$, R$''^2$, R$''^3$ and R$''^4$, which may be identical or different, represent: a hydrogen atom, a linear or branched, saturated or unsaturated C$_1$–C$_4$ alkyl radical, the arrows indicating the positions of the substitutions in formula (c); k is an integer, preferably k=0 or 1.

Preferably, in the process according to the invention, the compound

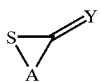

is chosen from:

2-oxo-4-thiazolidinecarboxylic acid, also known under the name procysteine:

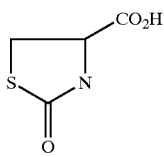

N-acetylhomocysteinethiolactone:

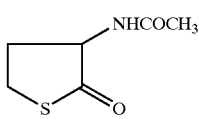

γ-thiobutyrolactone:

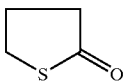

iminothiolane:

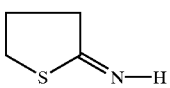

Advantageously, in the process according to the invention, a reactant chosen from procysteine, N-acetylhomocysteinethiolactone and γ-thiobutyrolactone is used.

Advantageously, in the process according to the invention, the compound

is γ-thiobutyrolactone.

γ-Thiobutyrolactone is a commercial product.

The reaction for opening the thiolactone or iminothiolane is generally carried out under inert atmosphere either in water or in an aromatic solvent such as toluene or an alcohol such as methanol, ethanol, isopropanol or butanol, and, depending on the boiling point of the solvent, at a temperature of between 0° C. and 110° C.

However, according to a preferred form of the invention, the reaction is carried out in water and, in this case, the dendrimer or the hyperbranched polymer and the thiolactone or the iminothiolane are mixed in stoichiometric proportions (relative to the functions —XH of the polymer) and the mixture is then brought, under inert atmosphere, to a temperature of between 0° C. and 110° C.

When it is desired to conserve the free amine or hydroxyl functions among the n functional groups of the hyperbranched polymer or of the dendrimer, the desired amount m of thiolactone or iminothiolane molecules per dendrimer molecule or per hyperbranched polymer molecule is used in order to obtain the dendrimer or the hyperbranched polymer having n-m free amine or hydroxyl functions and m thiol functions.

Depending on the basicity of the dendrimer or the hyperbranched polymer, the reaction time can be between 1 and 48 hours, the reaction progress being monitored by assaying the appearance of the thiol and/or the disappearance of the amine function or of the alcohol function. It is also possible to monitor the conversion of the starting polymer by electrophoresis.

Advantageously, when the radical —A— contains a free acid function or a free amine function, this function is neutralized before introducing the starting polymer into the reaction medium.

If, during the reaction, a certain amount of thiol is oxidized into the corresponding disulphide, the reaction mixture is then diluted with twice its volume of water and stirred in acidic medium in the presence of zinc powder for 1 to 3 hours. With most of the disulphide having been reduced, the mixture is then filtered and a solution of the expected compound is obtained, which can be used directly.

Dendrimers and hyperbranched polymers containing a mercaptoalkylamide function can also be obtained in a known manner by an amidation reaction of the corresponding mercaptoalkanoic acid or esters thereof. Such a process can be represented by the following reaction scheme:

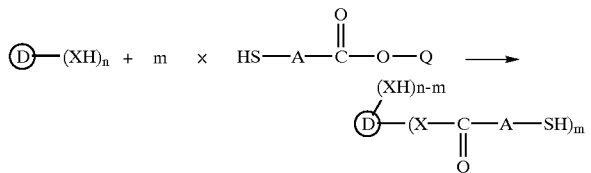

in which X, n, m, A and (D)

have the same meaning as above and Q represents a hydrogen atom or a saturated or unsaturated, linear or branched $C_1$–$C_{10}$ alkyl radical.

However, the preparation process described above starting with a thiolactone or an iminothiolane is faster and does not lead to the formation of side products that occasionally have a very unpleasant odour and contaminate the final product.

Reference may be made to the following documents which describe hyperbranched polymers and dendrimers in which the terminal group contains an amine function, the content of these documents being incorporated into the present description by reference: U.S. Pat. No. 4,694,064; U.S. Pat. No. 4,507,466; U.S. Pat. No. 4,631,337; U.S. Pat. No. 4,558,120; U.S. Pat. No. 4,568,737; U.S. Pat. No. 4,587,329; WO-A-9502008; WO-A-9314147; EP-234408; U.S. Pat. No. 4,289,872; U.S. Pat. No. 4,360,646; Proc. Natl. Acad. Sci. USA, 85, 5409–5413 (1988); WO95/02008; WO93/14147; J. Am. Chem. Soc. 117, 9764 (1195); FR-2, 734,268.

Dendrimers containing terminal groups bearing a primary amine function are polyamidoamines such as those sold under the trade name Starburst PAMAM by the company Dendritech (block copolymers of ethylenediamine and of methyl acrylate). They can also be chosen from polyalkylenepolyamine-type dendrimers such as, for example, the polyethyleneimines and polypropyleneimines manufactured by the company DSM and described in the patents: WO 93/14147 and WO 95/02008. They may also belong to the polylysine family, as described in U.S. Pat. No. 4,360,646. Among the hyperbranched polymers, mention may be made of polyalkylenepolyamines such as the polyethyleneimine sold by the company BASF under the brand names Polymin and Lupasol.

Hyperbranched polymers and dendrimers containing amine functional groups can also consist of a core and generations of base units, monomers or spindles, of any nature, on which an end group T bearing an amine function has been grafted.

Hyperbranched polymers and dendrimers containing hydroxyl end groups, in particular polymers of the polyester family, are described in the following documents, the content of which is incorporated into the present description by reference: U.S. Pat. No. 4,587,329; WO 93/17060; WO 92/14543; J. Am. Chem. Soc., 113, 4583–4588 (1991); Macromolecules 25, 4583–4587 (1992); U.S. Pat. No. 5,196,502; U.S. Pat. No. 5,214,122.

Preferably, the starting polymer is chosen from dendrimers.

After the reaction, the nature of the core and the branches of the starting polymer are not modified. Possibly, as a function of the proportions of reactants used, some of the starting end groups are not modified. Thus, if a polyamidoamine is used to begin with, which is treated with γ-thiobutyrolactone, the process of the invention gives a polyamide containing mercapto-4-butyramide end functions. Starting with a polyalkylenepolyamine, the process of the invention gives a polyalkylenepolyamine grafted with mercapto-4-butyramide functional groups. Starting with a polyester, the process of the invention gives a polyester containing mercapto-4-butyramide end functions.

These novel polymers have reductive properties and can be used in place of the reducing agents used conventionally, for example in cosmetic applications, such as, for example, treatment of the nails and the hair. In particular, these novel polymers can be used as reducing agents in permanent-waving compositions.

Since the polymers according to the invention contain an —SH end function, they can be used as preserving agents for protecting products that are particularly sensitive to oxidation. They can be used as antioxidants in compositions of any nature, especially in cosmetic or pharmaceutical compositions, for example in hair compositions, as shampoos, lotions, gels, emulsions or lacquers for the hair, rinse-out compositions, to be applied before or after shampooing, before or after dyeing or bleaching, before, during or after permanent-waving or straightening of the hair, styling or treating lotions or gels, lotions or gels for blow-drying or setting the hair, and permanent-waving, straightening, dyeing or bleaching compositions for the hair. They can also be used as antioxidants in skincare products or make-up products, such as products for making up the eyelashes, the eyebrows or the skin, such as an epidermal treatment cream, a foundation, a lipstick, an eyeshadow, a blusher, a mascara, an eyeliner or a nail varnish, or in skincare or skin cleansing lotions, creams and milks.

The subject of the invention is also a composition comprising, in a cosmetically or dermatologically acceptable support, at least one polymer according to the invention.

When applied to a support, the polymers according to the invention can form a film resulting from the formation of intermolecular disulphide bridges, thus leading to a polymer of the dendrimer or of the hyperbranched polymer containing —SH end functions.

This film can be formed from a few thiol functions, the other functions remaining free and being capable of having a reductive action.

The use of the polymers according to the invention as antioxidants can be envisaged directly in solution in the medium to be protected from oxidation, as is common with standard antioxidants such as thioglycolic acid, thiolactic acid or cysteine.

If the polymer is insoluble in the medium to be protected from oxidation, it is also possible to envisage fixing it, for example, in the form of a film or a pellet, to the walls or into the stopper of the bottle containing the formulation to be protected.

In this second case, the dendrimer or the hyperbranched polymer according to the invention can also be combined with a small amount of one of the mercaptans usually used as antioxidant, such as, for example, thioglycolic acid, thiolactic acid or cysteine. This combination thus makes it possible to limit the amount of soluble thiol in the composition to be protected and hence the usual drawbacks associated therewith—odour, changing of the colour—while at the same time retaining remarkable efficacy. The subject of the invention is thus also such a combination.

The hyperbranched polymers and dendrimers according to the invention have in particular the advantage of having a much fainter odour than the thiols usually used as antioxidants—they are virtually odourless at room temperature.

On account of their specific structure, the hyperbranched polymers and dendrimers according to the invention penetrate very little into keratin or into the epidermis, and they are thus relatively non-sensitizing and pose no toxicity problems.

Non-limiting examples will be given below by way of illustration.

EXAMPLES

Example 1

Dendrimer with an Ethylenediamine Core, an Ethylenediamine and Methyl Acrylate Spindle, of Generation 1, Having 8 Surface SH Functions 540 µl of γ-thiobutyrolactone (i.e. 1 equivalent calculated relative to all of the primary amine functions) are added to 2 grams of an aqueous solution at 55.7 g/100 g of dendrimer sold by the company Dendritech under the name PAMAM Starburst with an ethylenediamine core, of generation 1 (8 surface $NH_2$ functions), diluted with 2 ml of water, under an inert atmosphere at room temperature. The medium, which is initially heterogeneous, rapidly becomes homogeneous (1 hour). After stirring for 48 hours, only traces of γ-thiobutyrolactone are found in the medium. The mixture is washed 3 times with 10 ml of diethyl ether and nitrogen is then bubbled through the aqueous phase thus obtained in order to remove any trace of ether.

The aqueous solution thus obtained is analysed by NMR. It is observed that all the initial primary amine functions are in the form —NH—CO—$(CH_2)_3$—SH.

The active material content of this aqueous phase is 37.71 g/100 g. The dendrimer thus obtained is used as it is in aqueous solution.
Molar mass of the product synthesized: 2247 g.$mol^{-1}$
Empirical formula: $C_{94}H_{176}N_{26}O_{20}S_8$ Example 2

Dendrimer with an Ethylenediamine Core, an Ethylenediamine and Methyl Acrylate Spindle, of Generation 3, Having 16 Surface $NH_2$ Functions and 16 Surface SH Functions 384 µl of γ-thiobutyrolactone (i.e. 0.5 equivalent calculated relative to all of the primary amine functions) are added to 4 grams of an aqueous solution at 47.85 g/100 g of dendrimer sold by the company Dendritech under the name PAMAM Starburst with an ethylenediamine core, of generation 3 (32 surface $NH_2$ functions), diluted with 4 ml of water, under an inert atmosphere at room temperature. Upon addition, the heterogeneous medium rapidly becomes homogeneous (1 hour). After stirring for 20 hours, γ-thiobutyrolactone is no longer detected in the medium.

The aqueous solution thus obtained is analysed by NMR. It is observed that 50% of the initial primary amine functions are in the form —NH—CO—$(CH_2)_3$—SH.

The active material content of this aqueous phase is 27.75 g/100 g. The dendrimer thus obtained is used as it is in aqueous solution.
Molar mass of the product synthesized: 8532 g.$mol^{-1}$
Empirical formula: $C_{366}H_{704}N_{122}O_{76}S_{16}$ Example 3

Dendrimer with an Ethylenediamine Core, an Ethylenediamine and Methyl Acrylate Spindle, of Generation 1, Having 1.6 Surface $NH_2$ Functions and 6.4 Surface SH Functions 431 µl of γ-thiobutyrolactone (i.e. 0.8 equivalent calculated relative to all of the primary amine functions) are added to 2 grams of an aqueous solution at 55.7 g/100 g of dendrimer sold by the company Dendritech under the name PAMAM Starburst with an ethylenediamine core, of generation 1 (8 surface $NH_2$ functions), diluted with 2 ml of water, under an inert atmosphere at room temperature. The medium, which is initially heterogeneous, rapidly becomes homogeneous (1 hour). After stirring for 24 hours, γ-thiobutyrolactone is no longer detected in the medium.

The aqueous solution thus obtained is analysed by NMR. It is observed that 80% of the initial primary amine functions are in the form —NH—CO—$(CH_2)_3$—SH.

The active material content of this aqueous phase is 35.99 g/100 g. The dendrimer thus obtained is used as it is in aqueous solution.
Molar mass of the product synthesized: 2080.8 g.$mol^{-1}$
Empirical formula: $C_{87.6}H_{166.4}N_{26}O_{18.4}S_{6.4}$ Example 4

Branched Polyethyleneimine Polymer of Average Molecular Weight MW=1200, Having 6.75 SH Functions 1 gram of polyethyleneimine of average molecular weight MW=1200 sold by the company Polysciences is diluted in 3 grams of water and 482 µl of γ-thiobutyrolactone (i.e. 6.75 molar equivalents, calculated relative to the average molecular weight of the polymer) are then added at room temperature under an inert atmosphere. The medium, which is initially heterogeneous, rapidly becomes homogeneous (about 30 minutes). After stirring for 2 hours, γ-thiobutyrolactone is no longer detected in the medium. The aqueous phase gives a positive reaction after developing with sodium nitroprusside. It is thus observed that some of the initial primary amine functions are in the form of —NH—CO—$(CH_2)_3$—SH.

The active material content of this aqueous phase is 34.35 g/100 g. The dendrimer thus obtained is used as it is in aqueous solution.
Molar mass of the product synthesized: 1889.6 g.$mol^{-1}$

What is claimed is:
1. A polymer chosen from hyperbranched polymers and dendrimers containing at least one functional group of formula (I):

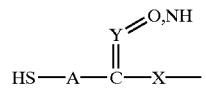

in which:
Y is chosen from an oxygen atom and an NH group;
A is chosen from linear, branched and cyclic, saturated and unsaturated $C_1$–$C_{12}$ alkanediyl groups, wherein said alkanediyl groups may or may not be interrupted by at least one heteroatom, and further wherein said alkanediyl group may or may not be substituted with at least one function chosen from amino groups NH$_2$ and salts thereof with inorganic acids or organic acids, acylamino groups NH—COR, in which R is chose from linear, branched and cyclic, saturated and unsaturated C$_1$–C$_{10}$ alkyl groups, C$_1$–C$_{10}$ alkylamino groups, carboxylic acid, and C$_1$–C$_{10}$ esters; and X is chosen from nucleophilic groups.

2. A polymer according to claim 1, wherein said alkanediyl groups are interrupted by at least one heteroatom chosen from O and N.

3. A polymer according to claim 1, wherein A is chosen from radicals of formulae (a) to (d) below:

  (a)

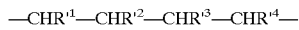  (b)

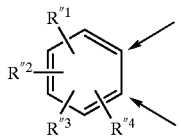  (c)

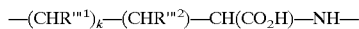  (d)

in which:

R$^1$, R$^2$, R$^3$, R$'^1$, R$'^2$, R$'^3$, R$'^4$, R$'''^1$ and R$'''^2$, each of which may be independently chosen from a hydrogen atom; linear, branched and cyclic, saturated and, unsaturated C$_1$–C$_6$ alkyl radicals; an amino radical; a carboxylic acid radical C$_1$–C$_{10}$ alkylamino radicals; and an acylamino radical NH—COR, in which R is chosen from linear, branched and cyclic, saturated and unsaturated C$_1$–C$_{10}$ alkyl groups;

R$''^1$, R$''^2$, R$''^3$ and R$''^4$, each of independently chosen from a hydrogen atom and linear and branched, saturated and unsaturated C$_1$–C$_4$ alkyl radicals;

wherein the arrows in formula (c) indicate the positions at which the compound of formula (c) is bonded to S— and —C of formula (I); and k is an integer.

4. A polymer according to claim 3, wherein k equals 0 or 1.

5. A polymer according to claim 3, wherein A it chosen from —CH$_2$—CH(CO$_2$H)—NH—, —(CH$_2$)$_2$—(CH$_3$CONH)CH—, and —(CH$_2$)$_3$— and Y is O; or A is —(CH$_2$)$_3$— and Y is NH.

6. A polymer according to claim 5, wherein A is —(CH$_2$)$_3$— and Y is O.

7. A polymer according to claim 1, wherein X is chosen from an oxygen atom and —NR'—, in which R' is chosen from a hydrogen atom; linear and branched, saturated and unsaturated C$_1$–C$_6$ alkyl groups; linear and branched, saturated and unsaturated C$_1$–C$_6$ monohydroxyalkyl groups and polyhydroxyalkyl groups; C$_1$–C$_6$ aminoalkyl groups; and polyalkyleneimine groups.

8. A polymer according to claim 7, wherein X is chosen from an oxygen atom and an —NH— group.

9. A polymer according to claim 1, wherein at least 10% of said nucleophilic groups X are grafted with a functional group having the following structure:

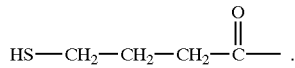

10. A polymer according to claim 9, wherein at least 40% of said nucleophilic groups X are grafted with a functional group having the following structure:

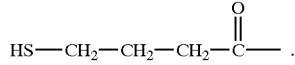

11. A polymer according to claim 1 wherein said polymer is a polyamide.

12. A polymer according to claim 1, wherein said polymer is a polyalkylenepolyamine.

13. A polymer according to claim 1, wherein said polymer is a polyethyleneimine.

14. A polymer according to claim 1, wherein said polymer is a polyester.

15. A polymer according to claim 1, wherein said polymer is a dendrimer.

16. A process for preparing a polymer, comprising reacting a thiolactone or an iminothiolane with a starting polymer chosen from hyperbranched polymers and dendrimers containing at least one end group containing at least one nucleophilic function or at least one chain containing at least one nucleophilic function according to the reaction scheme:

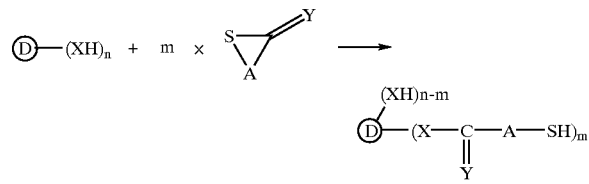

in which:

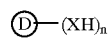

is chosen from dendrimers and hyperbranched polymers containing n nucleophilic functions XH;

X is chosen from nucleophilic groups;

n is greater than or equal to 2;

m is an integer less than or equal to n;

Y is chosen from an oxygen atom and an NH group; and

A is chosen from radicals of formulae (a) to (d) below:

  (a)

  (b)

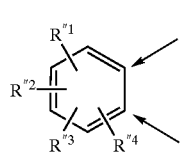  (c)

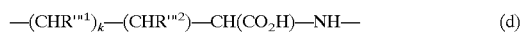  (d)

in which:

R$^1$, R$^2$, R$^3$, R$'^1$, R$'^2$, R$'^3$, R$'^4$, R$'''^1$ and R$'''^2$, each of which may be independently chosen from a hydrogen atom;

linear, branched and cyclic, saturated and unsaturated $C_1-C_6$ alkyl radicals; an amino radical; a carboxylic acid radical; $C_1-C_{10}$ alkylamino radicals; and an acylamino radical NH—COR, in which R is chosen from linear, branched and cyclic, saturated and unsaturated $C_1-C_{10}$ alkyl groups;

$R'''^1$, $R'''^2$, $R'''^3$ and $R'''^4$, each of which may be independently chosen from a hydrogen atom and linear and branched, saturated and unsaturated $C_1-C_4$ alkyl radicals;

wherein the arrows in formula (c) indicate the positions at which the compound of formula (c) is bonded to S— and —C of formula (I); and k is an integer.

17. A process according to claim 16, wherein k is 0 or 1.
18. A process according to claim 16, wherein

is chosen from:
procysteine:

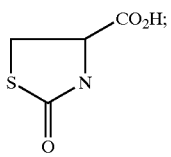

N-acetylhomocysteinethiolactone:

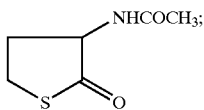

γ-thiobutyrolactone:

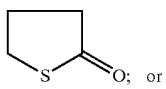

iminothiolane:

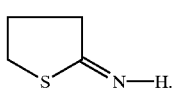

19. A process according to claim 18, wherein

is γ-thiobutyrolactone.

20. A process according to claim 16, wherein said reacting step is performed under an inert atmosphere in an aromatic solvent or in an alcohol solvent at a temperature ranging from 0° C. to 110° C.

21. A process according to claim 16, wherein said reacting step is performed under an inert atmosphere in water at a temperature ranging from 0° C. to 110° C.

22. A process for preparing a polymer, comprising reacting mercaptoalkanoic acid or a mercaptoalkanoic acid ester with a starting polymer chosen from hyperbranched polymers and dendrimers containing at least one end group containing at least one nucleophilic function or at least one chain containing at least one nucleophilic function, according to the reaction scheme:

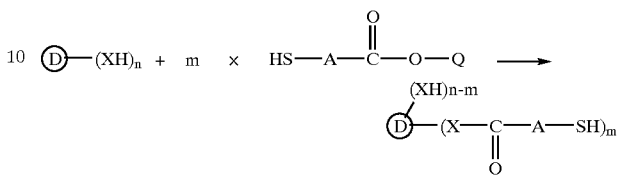

in which:

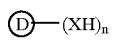

is chosen from dendrimers and hyperbranched polymers containing n nucleophilic functions XH;

X is chosen from nucleophilic groups;
m is an integer m less than or equal to n;
n is greater than or equal to 2;
A is chosen from linear, branched and cyclic, saturated and unsaturated $C_1-C_{12}$ alkanediyl groups, wherein said alkanediyl groups may or may not be interrupted by at least one heteroatom, and further wherein said alkanediyl group may or may not be substituted with at least one function chosen from:
amino groups $NH_2$ and salts thereof with inorganic acids or organic acids,
acylamino groups NH—COR, in which R is chosen from linear, branched and cyclic, saturated and unsaturated $C_1-C_{10}$ alkyl groups,
$C_1-C_{10}$ alkylamino groups,
carboxylic acid, and
$C_1-C_{10}$ esters; and
Q is chosen from a hydrogen atom and saturated and unsaturated, linear and branched $C_1-C_{10}$ alkyl radicals.

23. A composition comprising, in a cosmetically or dermatologically acceptable support, at least one polymer chosen from hyperbranched polymers and dendrimers containing at least one functional group of formula (I):

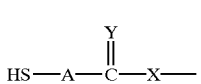

(I)

in which:
Y is chosen from an oxygen atom and an NH group;
A is chosen from linear, branched and cyclic, saturated and unsaturated $C_1-C_{12}$ alkanediyl groups, wherein said alkanediyl groups may or may not be interrupted by at least one heteroatom, and further wherein said alkanediyl group may or may not be substituted with at least one function chosen from
amino groups $NH_2$ and salts thereof with inorganic acids or organic acids,
acylamino groups NH—COR, in which R is chosen from linear, branched and cyclic, saturated and unsaturated $C_1-C_{10}$ alkyl groups,
$C_1-C_{10}$ alkylamino groups;
carboxylic acid, and
$C_1-C_{10}$ esters; and
X is chosen from nucleophilic groups.

24. A composition comprising at least one polymer and at least one compound chosen from thioglycolic acid, thiolactic acid and cysteine, wherein said at least one polymer is chosen from hyperbranched polymers and dendrimers containing at least one functional group of formula (I):

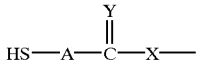

in which:
Y is chosen from an oxygen atom and an NH group;
A is chosen from linear, branched and cyclic, saturated and unsaturated $C_1$–$C_{12}$ alkanediyl groups, wherein said alkanediyl groups may or may not be interrupted by at least one heteroatom, and further wherein said alkanediyl group may or may not be substituted with at least one function chosen from:
  amino groups $NH_2$ salts thereof with inorganic acids or organic acids,
  acylamino groups NH—COR, in which R is chosen from linear, branched and cyclic, saturated and unsaturated $C_1$–$C_{10}$ alkyl groups,
  carboxylic acid,
  $C_1$–$C_{10}$ alkylamino groups, and
  $C_1$–$C_{10}$ esters; and
X chosen from nucleophilic groups.

25. A cosmetic composition according to claim 24, wherein said composition further comprises a cosmetically acceptable support.

26. A method for treating a keratinous substance, said method comprising applying at least one polymer to said keratinous substance, wherein said at least one polymer is chosen from hyperbranched polymers and dendrimers containing at least one functional group of formula (I):

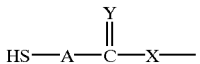

in which:
Y is chosen from an oxygen atom and an NH group;
A is from linear, branched and cyclic, saturated and unsaturated $C_1$–$C_{12}$ alkanediyl ,groups, wherein said alkanediyl groups may or may not be interrupted by at least one heteroatom, and further wherein said alkanediyl group may or may not be substituted with at least one function chosen from:
  amino groups $NH_2$; and salts thereof with inorganic acids or organic acids,
  acylamino groups NH—COR, in which R is chosen from linear, branched and cyclic, saturated and unsaturated $C_1$–$C_{10}$ alkyl groups,
  $C_1$–$C_{10}$ alkylamino groups,
  carboxylic acid, and
  $C_1$–$C_{10}$ esters; and
X is chosen from nucleophilic groups.

27. A method according to claim 26, wherein said keratinous substance is chosen from hair, nails, eyebrows, eyelashes and skin.

28. A method according to claim 27, wherein said keratinous substance is hair.

29. A method according to claim 28, wherein said method is a method for permanent waving of hair, and wherein said at least one polymer is applied to hair as a reducing agent.

30. A method for protecting from oxidation a product which is sensitive to oxidation, said method comprising including in said product at least one polymer chosen from hyperbranched polymers and dendrimers containing at least one functional group of formula (I):

in which:
Y is chosen from an oxygen atom and an NH group;
A is chosen from linear, branched and cyclic, saturated and unsaturated $C_1$–$C_{12}$ alkanediyl groups, wherein said alkanediyl groups may or may not be interrupted by at least one heteroatom, and further wherein said alkanediyl group may or may not be substituted with at least one function chosen from:
  amino groups $NH_2$ and salts thereof with inorganic acids or organic acids,
  acylamino groups NH—COR, in which R is chosen from linear, branched and cyclic, saturated and unsaturated $C_1$–$C_{10}$ alkyl groups,
  $C_1$–$C_{10}$ alkylamino groups,
  carboxylic acid, and
  $C_1$–$C_{10}$ esters; and
X is chosen from nucleophilic groups.

31. A method for protecting from oxidation a product which is sensitive to oxidation and which is contained in a container having walls and a cover, said method comprising either applying at least one polymer to the walls or cover of said container or placing at least one polymer in the form of a pellet in said container, wherein said at least one polymer is chosen from hyperbranched polymers and dendrimers containing at least one functional group of formula (I):

in which:
Y is chosen from an oxygen atom and an NH group;
A is chosen from linear, branched and cyclic, saturated and unsaturated $C_1$–$C_{12}$ alkanediyl groups, wherein said alkanediyl groups may or may not be interrupted by at least one heteroatom, and further wherein said alkanediyl group may or may not be substituted with at least one function chosen from:
  amino groups $NH_2$ and salts thereof with inorganic acids or organic acids,
  acylamino groups NH—COR, in which R is chosen from linear, branched and cyclic, saturated and unsaturated $C_1$–$C_{10}$ alkyl groups,
  $C_1$–$C_{10}$ alkylamino groups,
  carboxylic acid, and
  $C_1$–$C_{10}$ esters; and
X is chosen from nucleophilic groups.

32. A composition according to claim 23, wherein said composition is in the form of a hair composition chosen from shampoos; lotions; gels; emulsions and lacquers; rinse-out compositions to be applied before or after shampooing, bleaching or dyeing hair or before, during, or after permanent waving or straightening of hair; styling and treating lotions and gels, lotions and gels for blow-drying and setting the hair and permanent-waving, straightening, dyeing and bleaching compositions.

33. A composition according to claim 23, wherein said composition is in the form of a skin care or make up composition chosen from epidermal treatment cream, foundation, lipstick, eyeshadow, blusher, mascara, eyeliner, nail varnish, and skincare or cleansing lotions, creams and milks.

* * * * *

UNITED STATES PATENT AND TRADEMARK OFFICE
CERTIFICATE OF CORRECTION

PATENT NO.    : 6,395,867 B1
DATED         : May 28, 2002
INVENTOR(S)   : Jean Maignan It is certified that error appears in the above-identified patent and that said Letters Patent is hereby corrected as shown below:

Column 10,
Lines 55 and 56, in formula (I), delete " O,NH".
                                         //
Line 67, after "from", insert -- : --.

Column 11,
Line 3, replace "chose" with -- chosen --.
Line 34, after "saturated and", delete -- , --.
Line 36, after "acid radical", insert -- ; --.
Line 40, after "each of", insert -- which may be --.

Column 12,
Line 14, after "claim 1", insert --, --.

Column 13,
Line 45, replace "or" with -- and --.

Column 14,
Line 58, after "from", insert -- : --.

Column 15,
Line 19, after "$NH_2$", insert -- and --.
Line 43, after "A is", insert -- chosen --.
Line 44, replace ",groups," with -- groups, --.
Line 49, after "$NH_2$", delete -- ; --.

Signed and Sealed this

First Day of October, 2002

Attest:

Attesting Officer

JAMES E. ROGAN
Director of the United States Patent and Trademark Office